(12) United States Patent
Mohamed

(10) Patent No.: US 11,045,296 B1
(45) Date of Patent: Jun. 29, 2021

(54) DEVICE FOR MANAGING MALE URINARY INCONTINENCE AND REDUCING ERECTILE DYSFUNCTION

(71) Applicant: Adel W. Mohamed, Raleigh, NC (US)

(72) Inventor: Adel W. Mohamed, Raleigh, NC (US)

(*) Notice: Subject to any disclaimer, the term of this patent is extended or adjusted under 35 U.S.C. 154(b) by 0 days.

(21) Appl. No.: 17/214,142

(22) Filed: Mar. 26, 2021

Related U.S. Application Data

(60) Provisional application No. 63/004,800, filed on Apr. 3, 2020.

(51) Int. Cl.
*A61F 2/00* (2006.01)
*A61F 5/41* (2006.01)

(52) U.S. Cl.
CPC ............ *A61F 2/0054* (2013.01); *A61F 2/004* (2013.01)

(58) Field of Classification Search
CPC .................. A61F 5/41; A61F 2005/414; A61F 2005/415; A61F 2005/411; A61F 2/0054; A61F 2/004; A61F 5/005; A61F 5/0053; A61F 5/0056; A61F 5/003; A61F 2/0045; A61F 2/04; A61F 5/0033; A61F 5/0063; A61F 2250/0003; A61F 2/2442; A61F 2/2445; A61F 5/0083; A61H 19/32; A61H 9/0078; A61B 2017/00805; A61B 2017/00557; A61B 17/12; A61B 17/12031; A61B 17/12045
See application file for complete search history.

(56) References Cited

U.S. PATENT DOCUMENTS

| | | |
|---|---|---|
| 4,723,538 A | 2/1988 | Stewart et al. |
| 4,960,113 A | 10/1990 | Seeberg-Elverfeldt |
| 5,295,946 A | 3/1994 | Collins |
| 6,805,662 B2 | 10/2004 | Shah et al. |
| 7,377,896 B2 | 5/2008 | Dykers, Jr. |
| 9,956,109 B2 | 5/2018 | Hahr et al. |
| 10,398,586 B2 | 9/2019 | Tucker |
| 2003/0136415 A1 | 7/2003 | Lanton |
| 2017/0135895 A1 | 5/2017 | Jafri |
| 2018/0228639 A1 | 8/2018 | Hibri |

*Primary Examiner* — Christine H Matthews
(74) *Attorney, Agent, or Firm* — Neo IP

(57) ABSTRACT

A device operable to reduce the effects of erectile dysfunction and urinary incontinence in males which includes at least two inflatable chambers which encircle a portion of the penis. The two inflatable chambers are operable to constrict at least one vein of the penis in order to limit the flow of blood out of the penis via the at least one vein. The at least two inflatable chambers are also operable to maintain positioning of the device on the penis and to constrict the urethra in order to limit the flow of urine out of the penis.

20 Claims, 12 Drawing Sheets

DEVICE FOR MANAGING MALE URINARY INCONTINENCE AND REDUCING ERECTILE DYSFUNCTION

CROSS REFERENCES TO RELATED APPLICATIONS

This application claims priority to and the benefit of U.S. Provisional Application No. 63/004,800 filed Apr. 3, 2020, which is incorporated by reference in its entirety.

BACKGROUND OF THE INVENTION

The present invention relates to non-invasive medical devices, and more specifically to devices for managing of erectile dysfunction and urinary incontinence.

DESCRIPTION OF THE PRIOR ART

Prior art patent documents include the following:

U.S. Pat. No. 7,377,896 for inflatable penis ring by inventor Dykers, filed Jul. 25, 2006 and issued May 27, 2008, is directed to a device facilitating attachment of medical appliances to the penis. The device comprises an annular ring having an internal and external diameter. An array of inflatable balloons is evenly spaced around the internal diameter of the ring. A pressure control is provided to inflate or deflate the array of balloons as desired. Either air or liquid may be employed as an inflation medium. Inflation of the balloons, functions to efficiently and comfortably hold the ring in place on the penis. A rim or sleeve is mounted on the ring. Medical appliances may be attached to the rim.

U.S. Pat. No. 10,398,586 for apparatus for treating erectile dysfunction and enhancing penile enlargement by inventor Tucker, filed Aug. 18, 2017 and issued Sep. 3, 2019, is directed to an apparatus for enhancing erection of a penis including an expandable first member that partially encircles an upper portion of the penis and partially constricts at least a first vein of the penis to reduce the volume of blood carried away from the penis via the first vein. A second member is mounted to the first member includes left and right shoulder sections configured to contact the penis shaft along the left and right sides the urethra. A contoured section is formed between and extends outwards away from the shoulders so that, when the shoulder sections contact the penis shaft and the first member encircles at least partially encircles the upper portion of the penis, the contoured section extends over and does not constrict the urethra.

U. S. Publication No. 2003/0136415 for non-invasive erectile dysfunction aid by inventor Lanton, filed Jan. 19, 2002 and published Jul. 24, 2003, is directed to a non-invasive artificial erection apparatus for erectile dysfunction sufferers which has a semi-rigid tube with an inflatable bladder coupled to its inside wall. The apparatus also contains a valve and a pump for inflating the bladder through the valve. When inflated, the bladder forms a contracting lumen that provides pressure around the penile shaft to provide the artificial erection. The valve allows the bladder to substantially deflate the bladder for removal of the apparatus, or incrementally deflate to adjust the pressure of the bladder for comfort during intercourse. Other aspects of the erectile dysfunction aid include, inter alia, peristaltic inflation of the bladder to help congregate blood around the penile end, the ability to adjust the length of the apparatus by unrolling (or re-rolling) the distal end of the apparatus, which integrates the tube and bladder.

U.S. Pat. No. 6,805,662 for urinary incontinence control device and method of use by inventors Shah, et al., filed Feb. 18, 2003 and issued Oct. 19, 2004, is directed to a male urinary incontinence control device including a circumferentially continuous inflatable cuff having a plurality of inflatable passages therein, optionally reinforced by rigid members, that slips over the glans of the penis for positioning along the longitudinal axis of the penile shaft. Upon inflation, the cuff applies radially inwardly directed compressive force to the shaft of the penis with a concomitant restriction of the urethral passageway. The inflatable cuff includes an integrated hand pump for convenient inflation and deflation.

U.S. Pat. No. 5,295,946 for external penile erection device by inventor Collins, filed Nov. 18, 1992 and issued Mar. 22, 1994, is directed to a device for affecting or enhancing erection of the penis which comprises an external inflatable cuff which encircles the shaft of the penis at its base and extends distally. The cuff is provided with a plurality of volume expandable annular spaces arranged parallel to one another. The spaces are filled with fluid under pressure from a squeeze bulb to affect a tourniquet action. The spaces are inflated sequentially in a proximal to distal direction. As the spaces become sequentially pressurized, the inner diameter of the cuff is reduced, constricting the penis and trapping blood within the shaft and forcing it distally to thereby increase the rigidity of the penis.

U. S. Publication No. 2018/0228639 for external penile erection system by inventor Hibri, filed Feb. 13, 2018 and published Aug. 16, 2018, is directed to a system for affecting, augmenting, or enhancing erection of the penis which includes an elastomeric sleeve designed to comfortably and securely encircle the base of the penis. The sleeve is provided with a pair of inflatable chambers, a dorsal insert, and a ventral insert which are configured to apply focal pressure on the dorsal penile veins, while avoiding undue constriction of the corpora cavernosa or compression of the urethra, dorsal penile arteries, or nerves. The system includes fluid transfer apparatus having a reservoir for pressurized fluid, a pump, and valves for controlling the flow of fluid to the inflatable chambers. The system also includes an inflatable sealing apparatus which, when used in combination with a conventional vacuum erection tube, forms an airtight seal between the sleeve and the open end of the inflatable sealing member.

U.S. Publication No. 2017/0135895 for medical device for constricting venous outflow and for providing vibratory stimulus by inventor Jafri, filed Nov. 18, 2016 and published May 18, 2017, is directed to an apparatus for constricting blood flow and for providing vibratory stimulus to address erectile dysfunction. One implementation of the technology for enhancing erectile function, includes a single vibration unit or multiple vibration units. One implementation of the technology includes proximal and distal bands configured to annularly surround a penis close to the base of the penis and proximal to the distal glans penis. For one implementation of the technology, the two annular bands are connected by means of single or multiple intermediate bars, which house vibratory units. The intermediate bars are configured to partially cover a penis between the bands during use. One implementation of the device is made of an elastic, skin-compatible, slipper/smooth material.

U.S. Pat. No. 4,960,113 for erection aid by inventor Seeberg-Elverfeldt, filed Jan. 23, 1989 and issued Oct. 2, 1990, is direct to an erection aid which comprises an annular elastic tube which is inflatable to apply pressure to the base of the penis, reducing venous flow of blood while permitting arterial flow. A valve is provided for inflation. The annular tube is made with non-uniform wall thickness so that the inwardly facing portions of the wall are thinner and more easily deformable, permitting the desired pressure to be applied while minimizing axial deformation and thereby minimizing interference with normal functions. The thicker portions of the tube are sufficiently elastic to allow diametral increases as the penis becomes erect.

U.S. Pat. No. 4,723,538 for penile constrictor ring by inventors Stewart, et al., filed Oct. 16, 1986 and issued Feb. 9, 1988, is directed to a constrictor ring for the treatment and alleviation of impotence in males consisting of a ring-shaped elastic member operable to encircle the penis adjacent the user's torso, and including operating mechanism to expand it radially inwardly to engage and constrict the penis to inhibit the circulation of blood therein, thereby to encourage or maintain erection of the organ. The mechanism also includes devices for adjustably limiting the degree of constriction to which the organ may be subjected, for instantly removing all constriction if the user should feel pain or discomfort, and most importantly, for automatically releasing all constriction after a predetermined time delay sufficient to allow completion of an act of coitus, this release requiring no conscious act by the user, in order to avoid damage to the organ which otherwise could result if the user should fall asleep or otherwise fail to release the ring.

U.S. Pat. No. 9,956,109 for penile constriction device by inventors Hahr, et al., filed Sep. 7, 2012 and issued Mar. 1, 2018, is directed to a penile constriction device comprising a body including an aperture for surrounding a penis wherein the aperture defines an inner edge. An elastic strap is arranged within the aperture or at least in alignment with the aperture wherein the ends of the strap are connected to connection points at the inner edge of the aperture or at portions of the body adjacent to the aperture, and where in the connection points are positioned opposite to each other relative to the aperture and the length of the strap between its both ends is greater than the distance between the connection points so that the strap is able to be optionally brought into a first position so as to limit the aperture for defining a first aperture cross-section area or a second position opposite to the first position relative to the aperture so as to limit the aperture for defining a second aperture cross-section area which is larger than the first aperture cross-section area.

SUMMARY OF THE INVENTION

The present invention relates to non-invasive devices for reducing the effects of erectile dysfunction and urinary incontinence.

It is an object of this invention to improve the quality of life of individuals experiencing erectile dysfunction or urinary incontinence by restoring normal penile function as comfortably as possible.

In one embodiment, the present invention includes a penile compression device including a ring configured to fit around a penis, wherein the ring includes an outer layer, a corpora chamber, an inner layer, a soft pad, and a corpora valve, wherein the corpora chamber is positioned between the outer layer and the inner layer, wherein the inner layer encircles the entirety of the ring, wherein the inside surface of the inner layer is completely covered by the soft pad, wherein the corpora chamber is inflatable, wherein the corpora valve is configured to receive a fluid, and wherein the corpora chamber is configured to inflate when the corpora valve receives the fluid.

In another embodiment, the present invention includes a penile compression device including a ring configured to fit around a penis, wherein the ring includes an outer layer, a urethra chamber, an inner layer, a soft pad, and a urethra valve, wherein the urethra chamber is positioned between the outer layer and the inner layer, wherein the inner layer includes a gap, wherein the gap is adjacent to the urethra chamber, wherein the gap is operable to receive the soft pad, wherein the urethra chamber is inflatable, wherein the urethra valve is configured to receive a fluid, wherein the urethra chamber is configured to inflate when the urethra valve receives the fluid, and wherein the urethra chamber is configured to create compression on the penis near the urethra.

In yet another embodiment, the present invention includes a penile compression device including a ring configured to fit around a penis, wherein the ring includes an outer layer, a corpora chamber, a urethra chamber, an inner layer, a soft pad, a corpora valve, and a urethra valve, wherein the corpora chamber and the urethra chamber are positioned between the outer layer and the inner layer, wherein the inner layer encircles the entirety of the ring, wherein the inside surface of the inner layer is completely covered by the soft pad, wherein the corpora chamber and the urethra chamber are inflatable, wherein the corpora valve and the urethra valve are configured to receive a fluid via a pump, wherein the corpora chamber and the urethra chamber are configured to inflate when the corpora valve and the urethra valve receive the fluid, wherein the urethra chamber is configured to put pressure on the penis near the urethra, and wherein the corpora chamber is configured to create pressure on a dorsal vein of the penis when filled with the fluid.

These and other aspects of the present invention will become apparent to those skilled in the art after a reading of the following description of the preferred embodiment when considered with the drawings, as they support the claimed invention.

DETAILED DESCRIPTION

Figure 1:
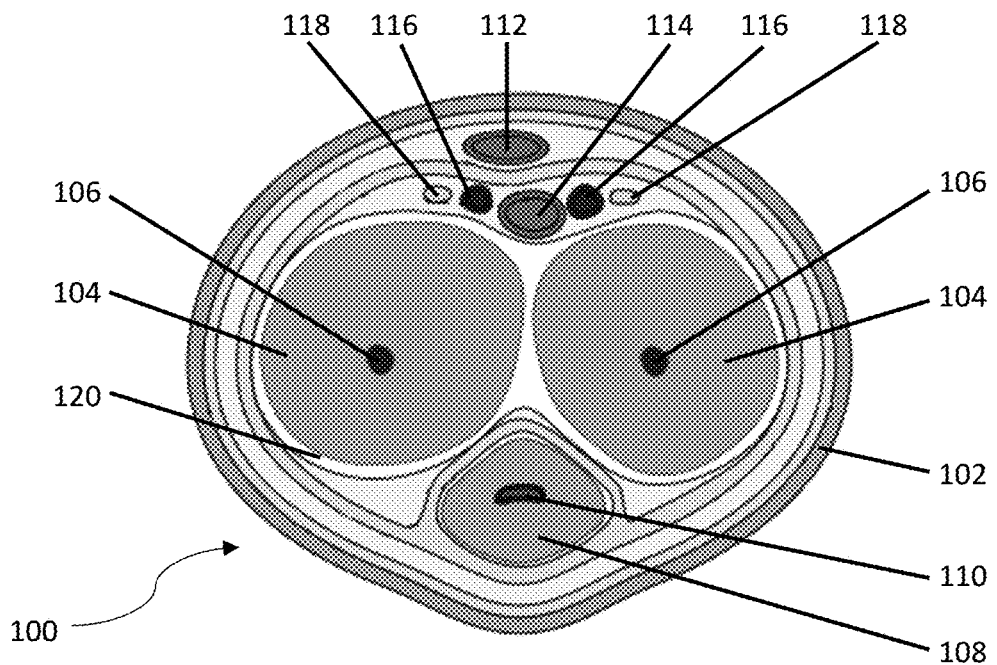
FIG. 1 illustrates a cross-section of the normal male penile anatomy.

The present invention is generally directed to non-invasive medical devices, and more specifically to devices for managing erectile dysfunction and urinary incontinence. The present invention includes a non-generic arrangement of inflatable and deformable chambers which independently compress the corpora and urethra to restrict outflow of blood from the penis and restrict the flow of urine through the urethra away from the bladder. The present invention provides males experiencing erectile dysfunction (ED) and/or urinary incontinence (UI) with a non-medicinal and non-lifestyle changing solution which is physically more comfortable, easier to use, and more versatile than the devices taught by the prior art.

In one embodiment, the present invention includes a penile compression device including a ring configured to fit around a penis, wherein the ring includes an outer layer, a corpora chamber, an inner layer, a soft pad, and a corpora valve, wherein the corpora chamber is positioned between the outer layer and the inner layer, wherein the inner layer encircles the entirety of the ring, wherein the inside surface of the inner layer is completely covered by the soft pad, wherein the corpora chamber is inflatable, wherein the corpora valve is configured to receive a fluid, and wherein the corpora chamber is configured to inflate when the corpora valve receives the fluid.

The penile compression device further includes wherein the ring is configured to expand to a volume of between about 20 cm$^3$ and about 35 cm$^3$. The penile compress device further includes wherein the corpora chamber is configured to create compression on a dorsal vein of the penis when filled with the fluid. The penile compress device further including wherein the soft pad is configured to distribute pressure across the bottom side of the penis. The penile compression device further including wherein the outer layer, the corpora chamber, and the inner layer are a concentric shape. The penile compression device further including wherein the corpora valve includes a quick release mechanism. The penile compression device further including wherein the outer layer is not expandable. The penile compression device further including wherein the inner layer includes a material, wherein the material includes felt, wool, cotton, polyester, foam, spandex, polyacrylic, polypropylene, silk, velvet, rayon, linen, leather, rubber, and/or silicone. The penile compression device further including wherein the corpora valve is self-inflatable. The penile compression device further including wherein the corpora chamber is configured to create a pressure between about 30 millimeters of mercury and about 120 millimeters of mercury on the penis.

In another embodiment, the present invention includes a penile compression device including a ring configured to fit around a penis, wherein the ring includes an outer layer, a urethra chamber, an inner layer, a soft pad, and a urethra valve, wherein the urethra chamber is positioned between the outer layer and the inner layer, wherein the inner layer includes a gap, wherein the gap is adjacent to the urethra chamber, wherein the gap is operable to receive the soft pad, wherein the urethra chamber is inflatable, wherein the urethra valve is configured to receive a fluid, wherein the urethra chamber is configured to inflate when the urethra valve receives the fluid, and wherein the urethra chamber is configured to create compression on the penis near the urethra.

The penile compression device further including wherein the outer layer, the urethra chamber, and the inner layer are a concentric shape. The penile compression device further including wherein the urethra valve includes a quick release mechanism. The penile compression device further including wherein the inner layer is configured to tangentially contact the skin of the penis when the urethra chamber is deflated. The penile compression device further including wherein the outer layer is not expandable. The penile compression device further including wherein the urethra chamber in a deflated position and the soft pad are configured to not contact the penis. The penile compression device further including wherein the inner layer includes a material, wherein the material includes at least one of felt, wool, cotton, polyester, foam, spandex, polyacrylic, polypropylene, silk, velvet, rayon, linen, leather, rubber, and/or silicone. The penile compression device wherein the urethra valve is self-inflatable.

In yet another embodiment, the present invention includes a penile compression device including a ring configured to fit around a penis, wherein the ring includes an outer layer, a corpora chamber, a urethra chamber, an inner layer, a soft pad, a corpora valve, and a urethra valve, wherein the corpora chamber and the urethra chamber are positioned between the outer layer and the inner layer, wherein the inner layer encircles the entirety of the ring, wherein the inside surface of the inner layer is completely covered by the soft pad, wherein the corpora chamber and the urethra chamber are inflatable, wherein the corpora valve and the urethra valve are configured to receive a fluid via a pump, wherein the corpora chamber and the urethra chamber are configured to inflate when the corpora valve and the urethra valve receive the fluid, wherein the urethra chamber is configured to put pressure on the penis near the urethra, and wherein the corpora chamber is configured to create pressure on a dorsal vein of the penis when filled with the fluid.

The penile compression device further includes wherein the corpora valve and the urethra value include a quick release mechanism.

None of the prior art discloses devices or methods utilizing devices which have multiple inflatable and deformable chambers which are concentric and together encircle the penis. Furthermore, none of the prior art discloses a soft pad operable to be positioned between an inflatable chamber and the skin of the penis in order to increase user comfort. Furthermore, the present invention provides an easy to use solution for individuals with a variety of conditions or symptoms but which does not create an emotional toll and is operable to be used discretely without creating pain or discomfort. The present invention also provides the advantage of adjusting the pressure inside each of the multiple chambers individually in order to achieve both individualized comfort and positive medical results. The present invention has quick release valve to enable individual to quickly release the device from the penis. When used to help individuals suffering from ED, the present device still allows for ejaculation when in use, a feature not present in the prior art.

Erectile dysfunction (ED) is not an uncommon condition, and results in men being unable to obtain or maintain an erection which is firm enough to provide satisfactory sexual intercourse. Regardless of whether an individual case of ED is an ongoing issue, it can lead to stress and self-confidence issues. ED can also be a sign of other underlying medical conditions, such as atherosclerosis, hypertension, diabetes and heart conditions. Current methods of managing and/or treating ED are commonly medicinal, psychological, involve physical treatment with vacuums and elastic rings, self-injection of medication into the penis, or in some cases surgery using penile implants. Other systems involve clamps or rings that are placed on the base of the penis to prevent blood from returning to the body, thus helping to maintain an erection. These clamps or rings can be used as stand-alone devices, in combination with medication self-injection, or with vacuum erection devices.

Male Urinary Incontinence (UI) is also not an uncommon problem, and results in the involuntary leakage of urine. Male UI can be a very embarrassing condition that often leads to lifestyle changes and severe psychological distress. There are different types of male UI. The most common type is stress urinary incontinence (SUI), which usually occurs as a result of weakness of the urinary sphincter, a set of muscles which prevents urine leakage in healthy individuals. In SUI, urine leaks upon any physical stress, such as sudden movement or cough. SUI is a common problem after prostate cancer surgery but also sometimes occurs following surgery for benign prostate enlargement or as a result of other underlying medical conditions. The second type of male UI is the total complete loss of urine control all the time. This is often a result of severe weakness of the urinary sphincter. The third type of UI is urgency incontinence which usually is the result of an overactive bladder. Male UI is also sometimes a symptom of other diseases including urinary tract infections, prostate gland infections, diabetes and neurological disorders. Current methods of managing and/or treating UI involve treating the underlying causes, strengthening the pelvic muscles, lifestyle changes including timed voiding, and in severe cases, surgical implantation of an artificial urinary sphincter. Penile clamps or rings are useful tools to aid in SUI and total incontinence cases that help in preventing urinary leakage and improving the individual's psychological well-being.

There are a variety of current methods of managing and/or treating ED which include medicinal, psychological, lifestyle, and physical treatments. For example, there are drugs administered orally or directly to the penis which are available but are also often abused by men who are simply seeking a longer-lasting erection. Some of these drugs include phosphodiesterase type-5 inhibitors, testosterone therapy, and vasodilators such as alprostadil. Common lifestyle changes recommended by physicians treating ED include the cessation of smoking, the limitation of alcohol consumption, increasing physical activity to promote a healthy body weight, and a better diet. Physicians sometimes also suggest treatment of emotional problems, such as relationship problems, depression, and analysis of other stressors in life. Physical treatments of ED include externally-applied devices such as vacuum-constriction devices and elastic rings. Vacuum-constriction devices generally have a cylindrical chamber which encircles the penis, a vacuum pump, and a constriction band, male truss, or clip. Vacuum-constriction devices are difficult to use as they involve many steps, are often too tight and are painful to apply and remove, and in some cases create added stress for the user and/or their sexual partner. Elastic rings are also often used by males, as they constrict blood flow within the penis to help maintain a longer erection. However, these devices are not always comfortable due to sensitivity of the underside of the penis and the urethra, and are limited by size and different user needs. Some physical treatments for ED are surgical. This includes the implantation of a prosthesis, which has historically taken many forms, including pairs of inflatable and distensible tubes and malleable rods. Many men find a surgical procedure to be intimidating and often not an option for them, and instead hope to find release from aforementioned methods.

The main volume of the penile shaft is comprised of the corpus cavernosum, of which there are two columns, and the corpus spongiosum. The urethra travels through the corpus spongiosum. The corpus cavernosum and corpus spongiosum, hereafter referred to as a whole as the corpora, fill with blood when the brain sends a stimulus to the penile vessels causing them to relax, bringing more blood into the corpora and causing the corpora to expand and to compress the veins which normally allow blood to drain. When the brain sends a stimulus to reverse the erection, the surrounding penile vessels contract to prevent further blood flow into the corpora, and blood is able to leave the corpora by way of the veins in the penis, causing the penile shaft to revert to the flaccid state. A device which prevents blood from exiting the corpora will necessarily assist in obtaining an erection and in maintaining an erection for a longer period of time.

There are also a variety of methods for managing and/or treating UI, many of which depend on the degree to which it impacts the life of the individual. Many methods are lifestyle changes, including reducing daily caffeine intake and alcohol consumption, eating a higher fiber diet, cessation of smoking, maintaining a healthy weight, timed voiding of the bladder, and double voiding of the bladder. Some physicians are also known to recommend exercises such as pelvic muscle exercises to strengthen the muscles used to stop urinating, and this is sometimes combined with biofeedback sensors to help individuals regain control over the relevant muscles. Physicians also prescribe medications to combat UI, which include anticholinergics to calm an overactive bladder, mirabegron to treat urge incontinence, and alpha blockers to relax bladder neck muscles. Other methods include external collection systems such as a condom catheter and catheters for intermittent catheterization. In some individual cases, severe UI warrants surgical procedures including the placement of an indwelling catheter inserted through the urethra or through an incision in the abdomen. Another method for treating severe male UI is the surgical implantation of artificial urinary sphincter system which is composed of a cuff that surrounds the urethra and a reservoir that contains saline and a pump located under the scrotum skin. The cuff constricts the urethra all the time, preventing urine leakage. When the bladder is full and the individual feels the urge to urinate, he simply compresses the pump which causes the cuff to open and the urine to flow out. Two minutes later, the system automatically recycles itself and the cuff closes around the urethra to prevent further urine leakage. Many of these methods cause discomfort for a user, especially in the placement of a catheter of any type which provides opportunity for the growth of bacteria. Other commonly employed devices include straps, clamps, bands, and other cradling devices which are tightened around the penis in order to close the urethra. However, tightening the device enough to sufficiently close the urethra causes significant and frequent pain due to the amount of pressure applied in other areas, such as the corpora and surrounding nerves. The male urethra is the exit point of urine from the body. As such, a device which is able to compress and close off the urethra at any point is operable to treat UI.

Accordingly, there is a need for a device that provides pressure on the main body of the penis near the veins in order to prevent the backflow of blood, or pressure on the area of the urethra to prevent urine leakage, while providing increased comfort such that the device is operable to be worn by a male for extended periods of time without having to remove it often. Further, there is a need for a device for UI treatment that does not pose a risk of damage to dorsal nerves and the superficial dorsal vein.

Referring now to the drawings in general, the illustrations are for the purpose of describing one or more preferred embodiments of the invention and are not intended to limit the invention thereto.

FIG. 1 illustrates a cross-section of the normal male penile anatomy. In this cross-section of the penis 100, visible is the skin 102, the corpus cavernosum 104, of which there are two, the cavernous artery 106, of which there are two, the corpus spongiosum 108, the urethra 110, the superficial dorsal vein 112, the deep dorsal vein 114, the dorsal artery 116, of which there are two, and the dorsal nerve 118, of which there are two. Together, the corpus cavernosum 104 and the corpus spongiosum 108 make up the corpora. The tunica albuginea 120 surrounds the corpora cavernosa. The average penis has a circumference of about 4.0 inches (or about 10 centimeters). Other anatomical elements, such as the multiple layers of fascia, are not of relevance to the present invention and as such are not labeled here.

Figure 2A:
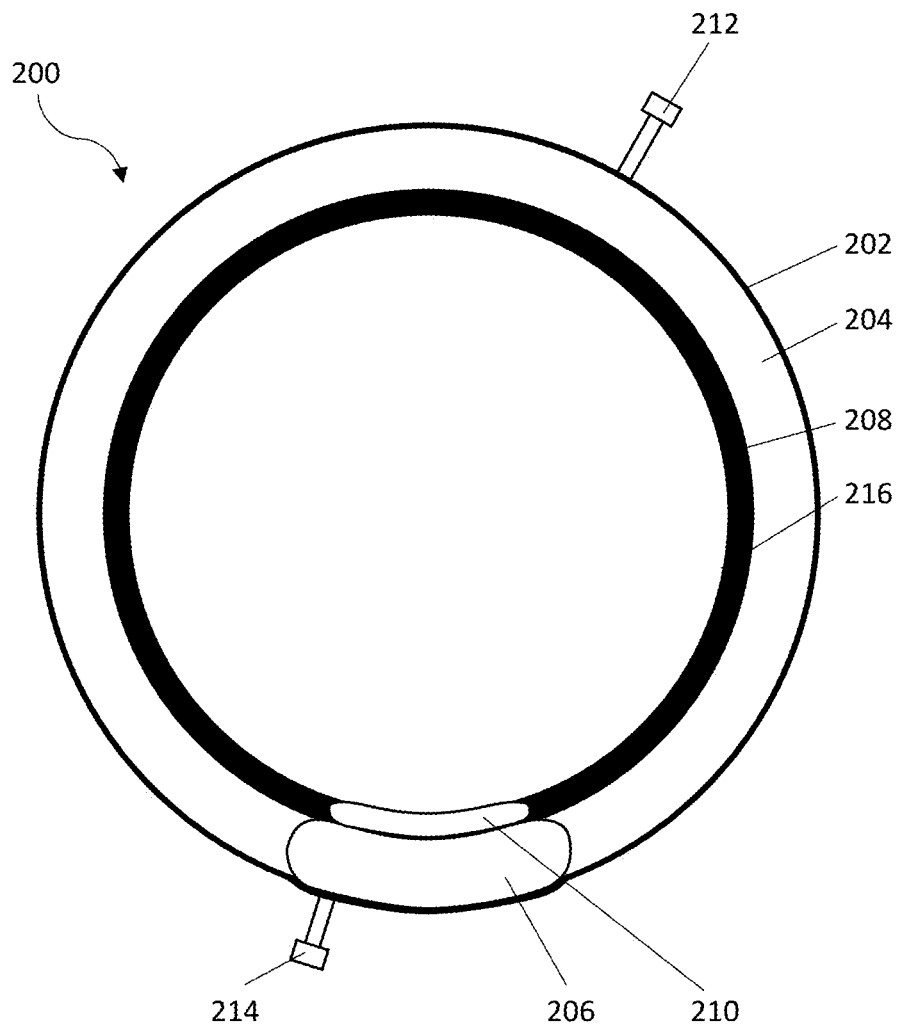
FIG. 2A illustrates a front orthogonal view of a device for managing male urinary incontinence and reducing erectile dysfunction, according to one embodiment of the present invention.
Figure 2B:
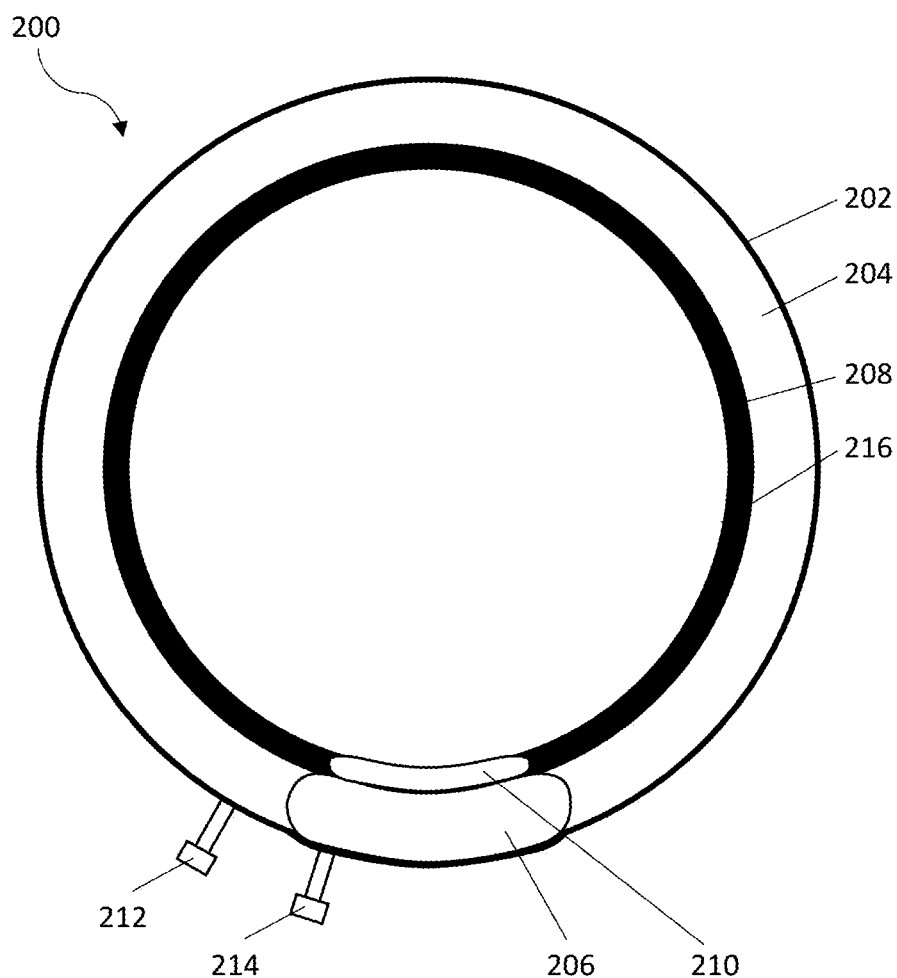
FIG. 2B illustrates a front orthogonal view of a device for managing male urinary incontinence and reducing erectile dysfunction, according to one embodiment of the present invention.

FIG. 2A illustrates a device for managing male urinary incontinence and reducing erectile dysfunction according to one embodiment of the present invention. The device is a ring 200 which is comprised of an outer layer 202, a corpora chamber 204, a urethra chamber 206, an inner layer 208, a soft pad 210, a corpora valve 212, and a urethra valve 214. The outer layer 202 and the inner layer 208 are concentric circles or an otherwise concentric shape, and the corpora chamber 204 and the urethra chamber 206 are secured between the outer layer 202 and the inner layer 208. In one embodiment the inner layer 208 does not make a complete circle, and there is a gap in the inner layer 208 adjacent to the urethra chamber 206. In an alternative embodiment, the gap in the inner layer 208 adjacent to the urethra chamber 206 is filled by the soft pad 210. The corpora chamber 204 and the urethra chamber 206 are inflatable and deformable chambers which are operable to be inflated by the corpora valve 212 and urethra valve 214, respectively. In one embodiment, corpora valve 212 and urethra valve 214 are on opposite sides of the ring 200. FIG. 2B illustrates an alternative embodiment of the present invention, wherein the corpora valve 212 and urethra valve 214 are on the same side of the ring 200 for easy access by the user. The ring 200 can be used facing in either direction such that the valves 212 and 214 are accessible to either the left or right hand of the user, whichever is preferred. The inner layer 208 is also elastic and deformable. The outer layer 202 is less expandable than the inner layer 208, and is also thicker, which forces the corpora chamber 204 to expand inwards when filled with water, air, or another fluid and as such, causes compression on the dorsal veins 112 and 114 to help sustain the erection. In another embodiment, the outer layer 202 is not expandable and does not expand. The outer layer of the urethral chamber 206 is less expandable than the adjacent soft pad 210 to allow the urethra chamber to expand inwards compressing the soft pad against the urethra to prevent urinary leakage.

In one embodiment, the outer layer 202 provides the majority of the structural integrity of the ring 200. The outer layer 202 has an inner and outer surface, wherein the circumference of the outer surface determines the external circumference and diameter of the ring 200. The inner surface of the outer layer is mated to the corpora chamber 204 and the urethra chamber 206 by chemical or physical means. In one embodiment, the outer layer 202 is mated to the corpora chamber 204 and the urethra chamber 206 at the interface of the inner surface of the outer layer and the corpora chamber 204 and the urethra chamber 206 using an adhesive such as glue. In another embodiment, the outer layer 202 is mated to the corpora chamber 204 and the urethra chamber 206 at the interface of the inner surface and the corpora chamber 204 and the urethra chamber 206 by chemical bonding. The outer layer 202 must provide a significant amount of strength to the ring 200 in order to resist substantial expansion when the corpora chamber 204 and/or the urethra chamber 206 are inflated around a penis 100. However, the outer layer 202 must also be compliant such that it maintains a high level of comfort for the user. In a preferred embodiment, the outer layer 202 is between about 2 millimeters thick. In an alternative embodiment, the outer layer 202 is between about 0.5 millimeters and about 3.0 millimeters thick. In yet another embodiment, the outer layer 202 is no more than about 5.0 millimeters thick. The outer layer 202 also establishes the size of the ring 200. In a preferred embodiment, the external surface of outer layer 202 has a circumference of about 8.13 inches (or about 20.7 centimeters). In an alternative embodiment, the outer layer 202 has a circumference of between about 7.0 inches and about 9.5 inches. In yet another embodiment, the outer layer 202 has a circumference of between about 5.0 inches and about 12.0 inches. In another embodiment, the outer layer 202 has a circumference of less than about 15.0 inches.

In a preferred embodiment, the outer layer 202 is made of an inelastic and flexible non-latex material that is operable to last for at least 6 months and withstand the pressure and wear and tear of use, as well as being washable. Preferably, the outer layer 202 is thicker than the inner layer 208. The length of the ring 200, or the distance that the ring 200 covers from the base of the penis towards the end of the penis, is sized to be comfortable for the largest number of males. However, the length of the ring 200 is operable to be changed. In a preferred embodiment, the ring 200 is about 0.4 inches (or about 1 centimeter) long. In an alternative embodiment, the ring 200 is between about 0.3 inches (or about 0.75 centimeters) and about 0.5 inches (or about 1.25 centimeters) long. In yet another embodiment, the ring 200 is between about 0.2 inches (or about 0.5 centimeters) and about 1.2 inches (or about 3.0 centimeters) long. In yet another embodiment, the ring is up to about 3.94 inches (or about 10.0 centimeters) long. In another embodiment, the outer layer 202 is covered by another layer of an inelastic material, such as an inelastic rubber, to prevent the outer layer 202, and the chambers inside it, from expanding outwards.

The circumference of an average sized flaccid penis is about 4 inches (or about 10 centimeters). In one embodiment, the circumference of the inside surface 216 of the inner layer 208 is about 5.3 inches (or about 13.45 centimeters) such that there is an average clearance of about 5.5 millimeters between the inside surface 216 of the inner layer 208 and the skin 102 of the penis 100. In an alternative embodiment, the circumference of the inside surface 216 of the inner layer 208 is between about 4.0 inches (or about 10 centimeters) and about 6.0 inches (or about 15 centimeters) such that there is an average clearance of between about zero millimeters and about 7.95 millimeters between the inside surface 216 of the inner layer 208 and the skin 102 of the penis 100. In yet another embodiment, the circumference of the inside surface 216 of the inner layer 208 is between about 3.0 inches (or about 7.5 centimeters) and about 10 inches (or about 25 centimeters) and there is up to about 25 millimeters between the inside surface 216 of the inner layer 208 and the skin 102 of the penis 100.

In a preferred embodiment, the corpora chamber 204 is between about 7 millimeters and about 10 millimeters thick when uninflated. In another embodiment, corpora chamber 204 is between about 5 millimeters and about 15 millimeters thick when uninflated. In yet another embodiment, corpora chamber 204 is less than about 25 millimeters thick when uninflated. As such, in a preferred embodiment, the total volume of the ring 200 when not inflated, which consists primarily of the corpora chamber 204, is about 19.62 cubic centimeters (CCs), wherein the uninflated volume of the corpora chamber 204 is about 16.92 CCs. In an alternative embodiment, the total volume of the ring 200 when not inflated is between about 15 CCs and 25 CCs. In yet another embodiment, the total volume of the ring 200 when not inflated is between about 10 CCs and 35 CCs.

Figure 3:
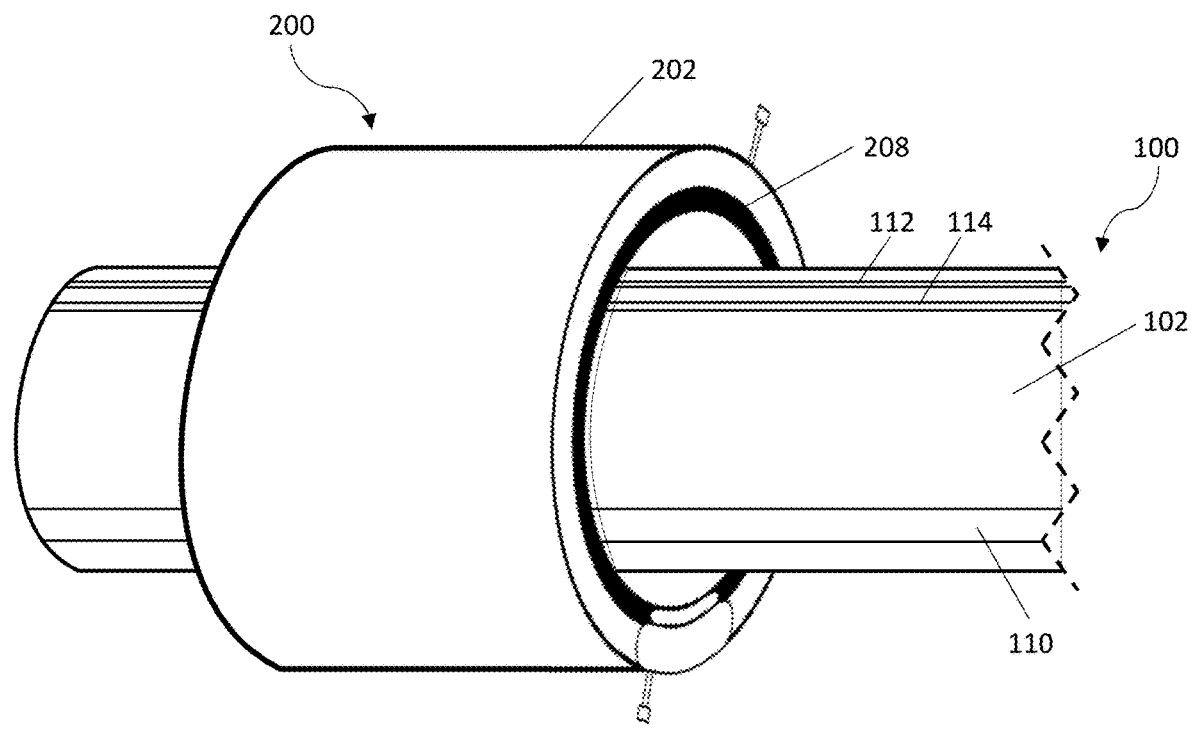
FIG. 3 illustrates a side perspective view of a device for managing male urinary incontinence and reducing erectile dysfunction positioned on the outer circumference of a partially flaccid male penis, according to one embodiment of the present invention.

FIG. 3 illustrates one embodiment of the ring 200 in use and prior to inflation of the corpora chamber 204 and the urethra chamber 206. The ring 200 is operable to be placed over a penis 100 such that it is movable and adjustable. When neither the corpora chamber 204 nor the urethra chamber 206 is inflated, the inside surface 216 of the inner layer 208 of the ring 200 only tangentially contacts the skin 102 of the penis 100 in one location. In a preferred embodiment, the ring 200 is placed onto the penis 100 when the penis is flaccid. Because it is loose, the ring 200 is operable to be easily removed from the penis 100 and further placed in a location that will be of the most comfort to the user. In a preferred embodiment, the ring 200 is placed at the base of the penis 100 for use. In an alternative embodiment, the ring 200 is placed no more than about 3.0 centimeters (or about 1.2 inches) from the base of the penis 100 for use. FIG. 3 further illustrates the urethra 110 as it is located towards the bottom of the penis 100 in normal male anatomy. Also illustrated in FIG. 3 are the superficial dorsal vein 112 and deep dorsal vein 114. The two dorsal arteries 116 and two dorsal nerves 118 are not pictured but are lateral to the deep dorsal vein 114, with one of each of the dorsal artery 116 and dorsal nerve 118 on either side of the deep dorsal vein 114. Also not pictured are the two cavernous arteries 106, one of which is centrally located in each corpus cavernosum. The positioning of the superficial dorsal vein 112 and deep dorsal vein 114 towards the top of the penis 100 and very close to the skin 102 allows for the ring 200 to place pressure on superficial dorsal vein 112 and deep dorsal vein 114 to close them off and prevent blood from flowing out of the penis. Furthermore, the position of the dorsal nerves close to the surface of the penis 100 creates the risk of pain found in many prior art devices created for the treatment of both ED and UI which include a rigid and non-deformable or minimally-deformable structure to function. Preferably, the ring 200 is placed at the base of the penis 100 in order to create and maintain a maximum erection.

Figure 4A:
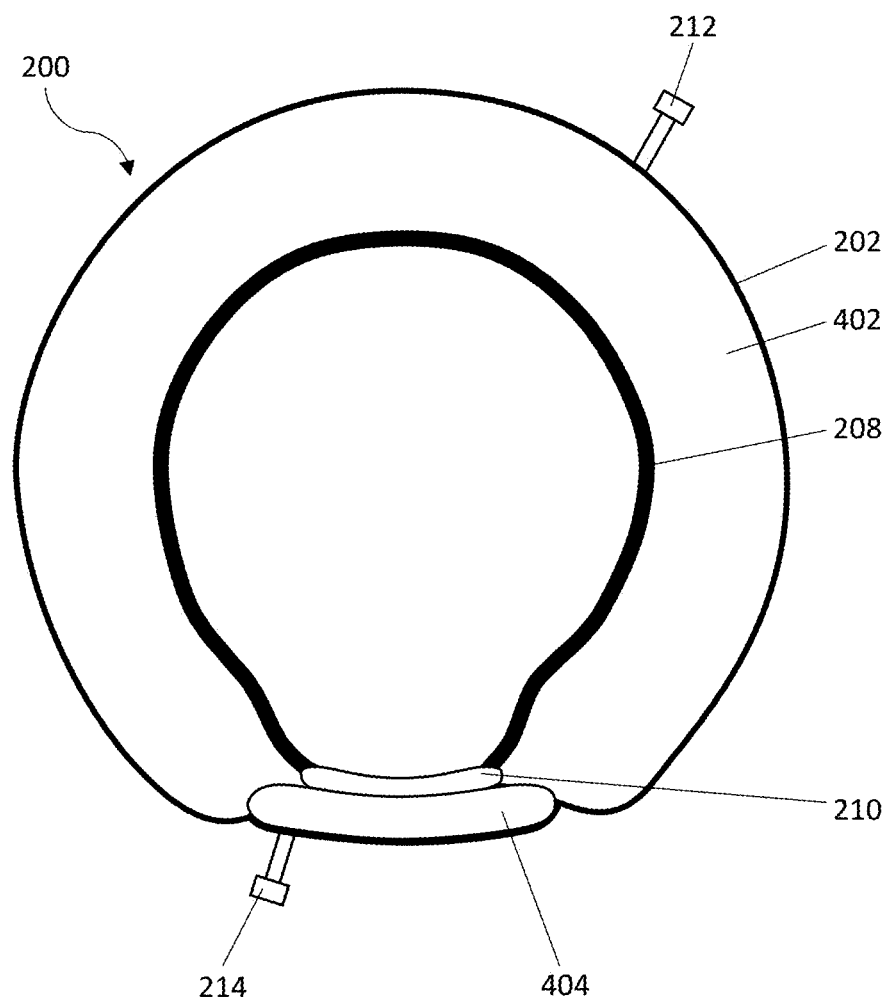
FIG. 4A illustrates a front orthogonal view of a device for managing male urinary incontinence and reducing erectile dysfunction having an inflated chamber, according to one embodiment of the present invention.
Figure 4B:
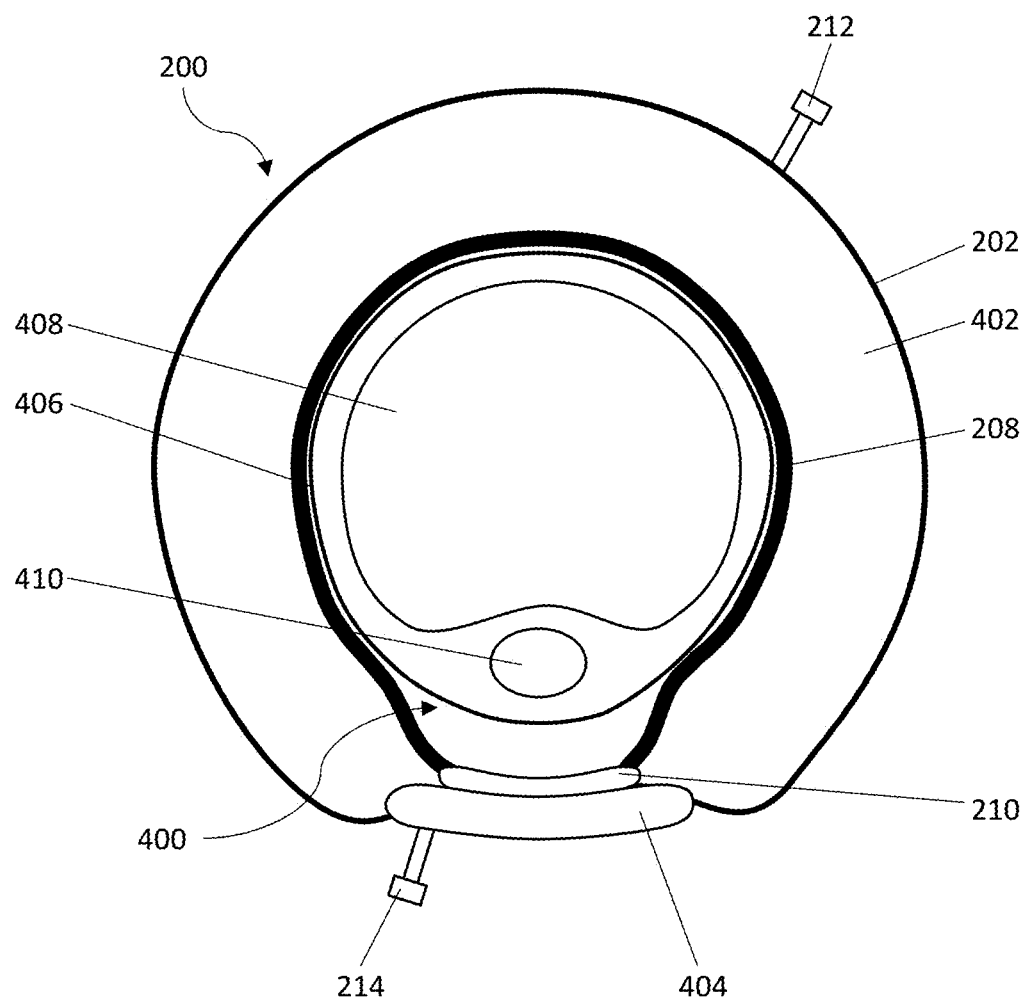
FIG. 4B illustrates a front orthogonal view of a device for managing male urinary incontinence and reducing erectile dysfunction having an inflated chamber which is positioned on an erect penis, according to one embodiment of the present invention.

In one embodiment, the ring 200 is used to treat ED by preventing blood from exiting the corpora cavernosa and corpus spongiosum tissues which is accomplished by putting pressure on and effectively closing the superficial dorsal vein 112 and deep dorsal vein 114. By preventing blood from exiting these tissues, the user is able to obtain an erection and maintain the erection for a longer period of time. In one embodiment, the corpora chamber 204 is inflated via the corpora valve 212 using water, air, or another fluid, and the inflated corpora chamber 402 has an increased volume, as demonstrated by FIG. 4A. The outer layer 202 is less compliant than the inner layer 208, so the inner diameter of the ring 200 decreases. When used to treat ED, the urethra chamber 206 is fully deflated, and the deflated urethra chamber 404 applies no pressure on the underside of the penis via the soft pad 210. In a preferred embodiment, neither the soft pad 210 nor the deflated urethra chamber 404 come into contact with the penis. FIG. 4B illustrates one embodiment of the device as it used to treat ED, illustrating the ring 200 surrounding an erect penis 400. The inside surface 216 of the inner layer 208 of the ring 200 is operable to contact the skin 406 of the erect penis 400, and the decreased diameter of the ring 200 is operable to put pressure on the erect penis 400 in order to compress the corpora 408 and resist outflow of blood. FIG. 4B further illustrates that the inside surface 216 of the inner layer 208 and soft pad 210 do not come into contact with the underside of the erect penis 400 near the open urethra 410.

Preferably, inflation of the inflated corpora chamber 402 imparts up between about 30 and about 120 millimeters of mercury (mmHg) of pressure on the penis 100, which is an amount of force operable to compress the superficial dorsal vein 112 and deep dorsal vein 114 but not so much that the dorsal arteries 116 are compressed or that the ring 200 would cause pain for the user. In one embodiment, the inflated corpora chamber 402 is operable to impart between about 10 mmHg and about 200 mmHg of pressure on the penis 100. In a preferred embodiment, between about 10 mmHg and about 200 mmHg of pressure is required to inflate the corpora chamber, and in another embodiment, between about 1 mmHg and about 500 mmHg is required to inflate the corpora chamber. The inflation of the corpora chamber closes the superficial dorsal vein 112 almost completely and closes the deep dorsal veins 114 partially, depending on the amount of force applied by the inflated corpora chamber 402. Further due to the inflated corpora chamber 402, the circumferences of the outer layer 202 and inner layer 208 are operable to change. In one embodiment, the circumference of the outer layer 202 increases by up to about 2 millimeters. In a preferred embodiment, the circumference of the outer layer 202 increases between about 0.1 millimeters and about 1.5 millimeters. In another embodiment, the circumference of the outer layer 202 increases up to about 100 millimeters, and in yet another embodiment, the circumference of the outer layer 202 does not increase at all. In one embodiment, the circumference of the inner layer 208 decreases by up to about 35.0 millimeters, or just enough to compress the penis 100. In another embodiment, the circumference of the inner layer 208 decreases by between about 20.0 millimeters and about 50.0 millimeters. In another embodiment, the circumference of the inner layer 208 decreases by up to about 100.0 millimeters. Changes in the circumference of the outer layer 202 and inner layer 208 are impacted by the size of the penis 100, the amount of pressure or fluid used to inflate the corpora chamber 204, and the materials used to construct the ring 200.

When inflated, the volume of the ring is increased substantially due to the introduced fluid such as water or air in order to close the gap between the ring 200 and the skin of the penis. In a preferred embodiment, the volume of the ring is expanded to about 26.1 CCs and the volume of the corpora chamber is about 23.4 CCs and has expanded by about 6.44 CCs. In another embodiment, the ring expands to a volume of between about 20 CCs and 35 CCs. In yet another embodiment, the volume of the ring expands to up to about 45 CCs.

Figure 5A:
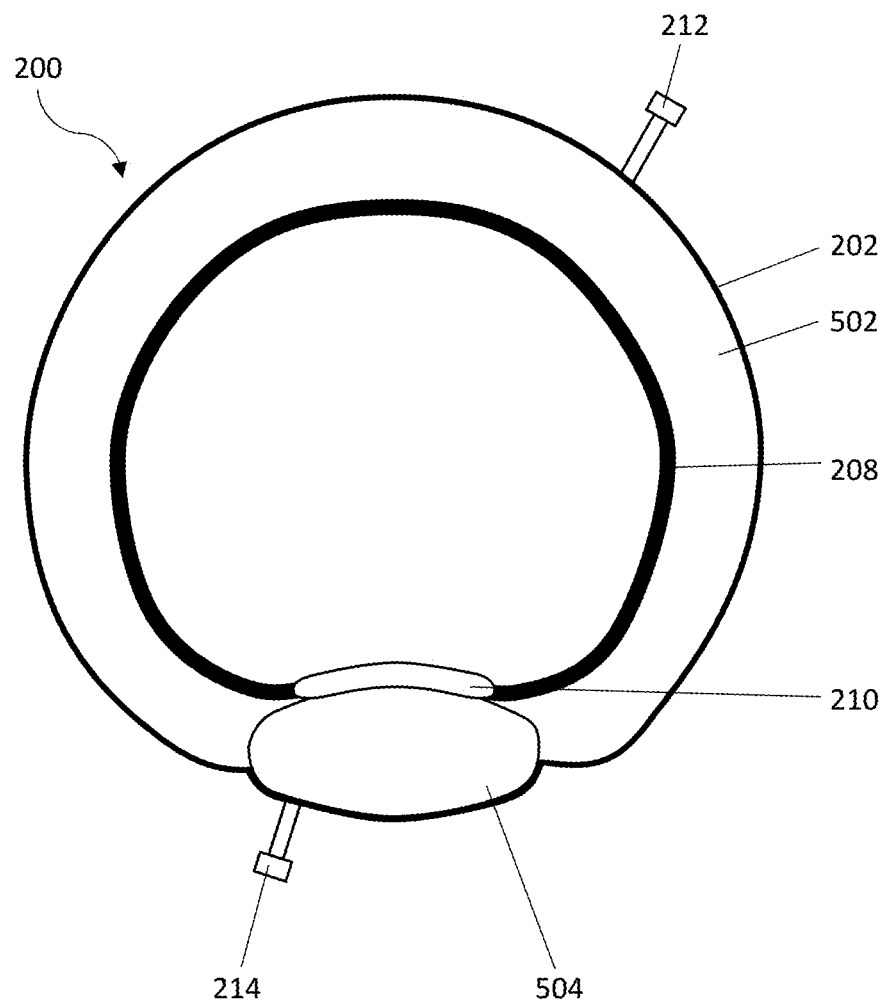
FIG. 5A illustrates a front orthogonal view of a device for managing male urinary incontinence and reducing erectile dysfunction having two inflated chambers, according to one embodiment of the present invention.
Figure 5B:
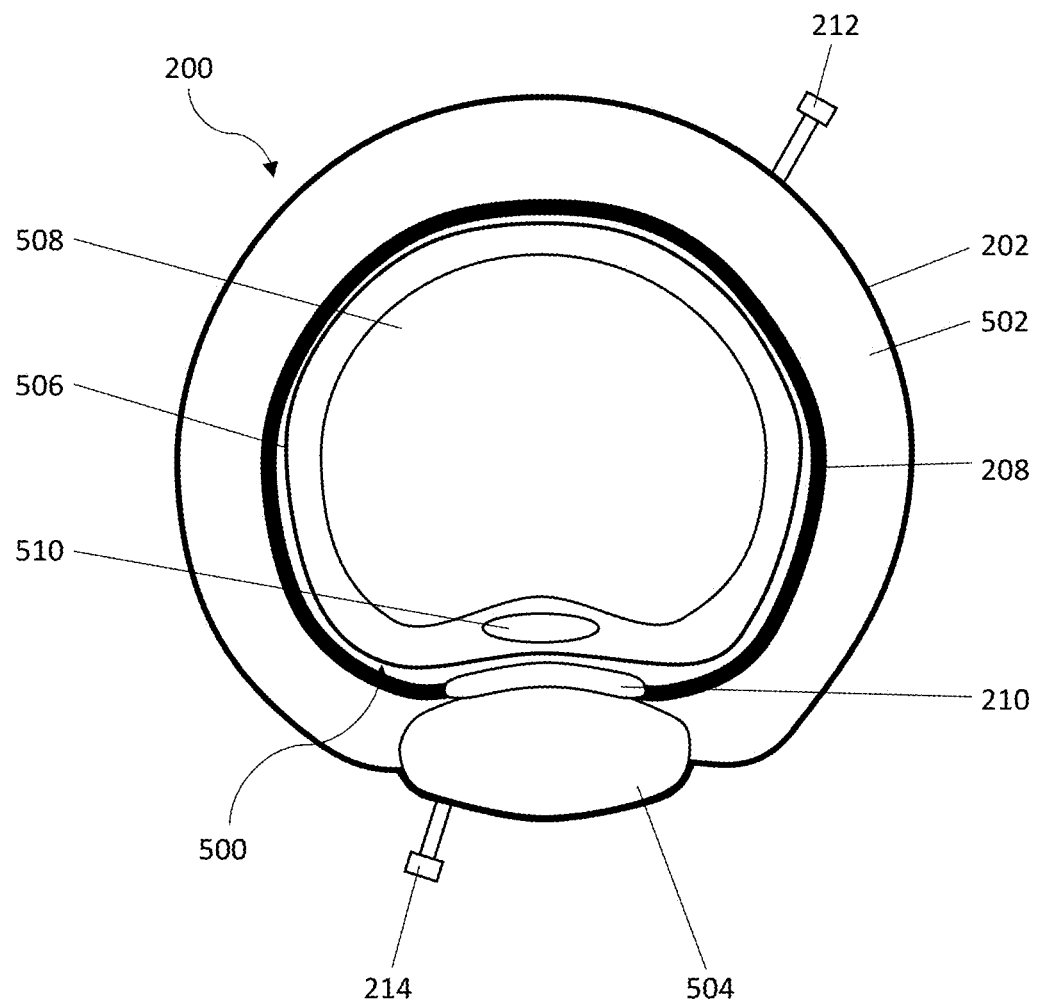
FIG. 5B illustrates a front orthogonal view of a device for managing male urinary incontinence and reducing erectile dysfunction having two inflated chambers which is positioned on a flaccid penis, according to one embodiment of the present invention.

In one embodiment, the ring 200 is used to mitigate UI by preventing urine from exiting the urethra. By compressing the urethra and stopping the flow of liquids, the user is able to lead a more normal life with decreased stressors or the use of other tools such as absorbent pads. In one embodiment, the corpora chamber 204 is partially inflated via the corpora valve 212, and the partially inflated corpora chamber 502 has an increased volume, as demonstrated in FIG. 5A. Due to the partially inflated corpora chamber 502, the ring 200 is operable to maintain its position on the penis 100 without creating undue pressure or discomfort. For example, the partially inflated corpora chamber 502 is inflated enough to come into contact with the skin of the penis such that the ring 200 cannot rotate, but not so much that the skin is able to be pinched, rubbed, or otherwise irritated. When used to treat UI, the urethra chamber 206 is then inflated, and the inflated urethra chamber 504 applies pressure to the underside of the penis by way of the soft pad 210. FIG. 5B illustrates one embodiment of the device as it is used to treat UI, illustrating the ring 200 surrounding a flaccid penis 500. The inside surface 216 of the inner layer 208 of the ring 200 is operable to contact the skin 506 of the flaccid penis 500 in order to prevent movement of the ring 200 such as, but not limited to, rotation, tilting, pinching, or sliding, as all of these motions cause discomfort and irritate the skin. In one embodiment, the corpora 508 maintains its natural flaccid volume. The inflated urethra chamber 504 applies pressure on the urethra 510 in order to close it and prevent the flow of urine.

Preferably, inflation of the partially inflated corpora chamber 502 imparts up to between about 20 mmHg and about 50 mmHg of pressure on the penis 100, which is an amount of force operable to secure the ring 200 on the penis 100 but not so much as to compress the superficial dorsal vein 112 and deep dorsal vein 114 or the dorsal arteries 116. In one embodiment, the partially inflated corpora chamber 502 is operable to impart between about 1 mmHg and about 100 mmHg of pressure on the penis 100. In a preferred embodiment, between about 10 mmHg and about 100 mmHg of pressure is required to partially inflate the corpora chamber 502, and in another embodiment, between about 1 mmHg and about 200 mmHg is required to partially inflate the corpora chamber 502. After partial inflation of the corpora chamber, the urethra chamber is operable to be partially inflated. The inflated urethra chamber 504 is inflated to an extent to which it is operable to completely close the urethra 510 and completely stop the leakage of urine. In one embodiment, the inflated urethra chamber 504 imparts between about 30 mmHg and about 80 mmHg of pressure on the penis near to the now closed urethra 510. In another embodiment, the inflated urethra chamber 504 imparts between about 10 mmHg and about 200 mmHg on the penis 100 near the urethra 510. In a preferred embodiment, between about 10 mmHg and about 100 mmHg is required to inflate the inflated urethra chamber 504, and in another embodiment, between about between about 1 mmHg and about 200 mmHg is required to partially inflate the urethra chamber 504.

Inner layer 208 provides the direct interface between the ring 200 and the penis. Inner layer 208 is also mated directly to the corpora chamber 204, and is mated by chemical or physical means. In one embodiment, inner layer 208 is mated to the corpora chamber 204 using an adhesive such as glue. In another embodiment, inner layer 208 is mated to the corpora chamber 204 by chemical bonding. In order to provide comfort and avoid creating irritation, inner layer 208 is made of a soft material, such as, but not limited to, felt, wool, cotton, polyester, foam, spandex, polyacrylic, polypropylene, silk, velvet, rayon, linen, natural or synthetic leather, rubber, silicone, or any other material that is soft to the touch, and combinations or blends of these materials, such that the inner layer 208 is operable to slide easily along the penis skin 102. In one embodiment, the inner layer 208 is produced from the same material as the outer layer 202. In an alternative embodiment, the inner layer 208 is produced from a different material than the outer layer 208. The inner layer 208 and the ring 200 as a whole are made of materials that allow the ring 200 to be hand washed with soap and water. The thickness of the inner layer 208 is also optimized to provide a high degree of compliance for user-specific anatomy. In a preferred embodiment, the inner layer 208 is between about 0.5 millimeters and about 1.0 millimeters thick. In an alternative embodiment, the inner layer 208 is between about 0.25 millimeters and about 2.0 millimeters thick. In yet another embodiment, the inner layer 208 is no more than about 3.0 millimeters thick. To provide an even greater degree of comfort, in one embodiment the ring 200, and specifically the inner layer 208, is molded and shaped specifically to the anatomy of the user. A specifically molded ring 200 is suited to avoid putting pressure on any areas of the individual's anatomy which are extraordinarily sensitive or otherwise abnormal.

The soft pad 210 provides an important interface with the penis because the skin 102 on the underside of the penis near the urethra 110 is very sensitive. The soft pad 210 provides a highly deformable, highly cushioned barrier between the pressure applied by the urethra chamber 206 and the penis. The soft pad 210 distributes pressure across the entirety of the bottom side of the penis 100 near the urethra 110 as opposed to placing pressure on only a small area of the underside of the penis 100, which would create increased pain and irritation for the user. The soft pad 210 is mated directly to the urethra chamber 206 by chemical or physical means. In one embodiment, the soft pad 210 is mated to the urethra chamber 206 using an adhesive such as glue. In an alternative embodiment, the soft pad 210 is mated to the urethra chamber 206 using chemical bonding. In one embodiment, the lateral ends of the soft pad 210 are connected directly to the inner layer 208 and do not interact directly with the urethra chamber 206 in order to provide flexibility as the shape and diameter of the ring 200 changes. In yet another embodiment, soft pad 210 is mated to both the inner layer 208 and the urethra chamber 206.

In order to provide comfort and avoid creating irritation, soft pad 210 is made of a soft material, such as, but not limited to, felt, wool, cotton, polyester, foam, spandex, polyacrylic, polypropylene, silk, velvet, rayon, linen, natural or synthetic leather, rubber, silicone, any other material that is soft to the touch, and combinations or blends of these materials such that the soft pad 210 is operable to increase the comfort of the ring 200 for the user. In one embodiment, the soft pad 210 is made from the same material as the outer layer 202 and/or the inner layer 208. In an alternative embodiment, the soft pad 210 is not made from the same material as the outer layer 202 or the inner layer 208. The thickness of the soft pad 210 is optimized to provide maximum comfort to the user regardless of whether the ring 210 is being used to tread ED or UI. In one embodiment, the soft pad 210 is between about 1.0 millimeters and about 2.0 millimeters thick. In another embodiment, the soft pad 210 is between about 0.5 millimeters and about 4.0 millimeters thick. In yet another embodiment, the soft pad 210 is no more than about 10.0 millimeters thick. In another embodiment, soft pad 210 is molded and shaped specifically to the anatomy of the user. A specifically molded soft pad 210, which is operable to be flat, close to flat, or concave in nature such as in a substantially parabolic shape or a parabolic shape having shoulders at each end, is suited to avoid putting any unnecessary pressure on any areas of specific individual's penis anatomy which are extraordinarily sensitive or otherwise abnormal. Like the remainder of the elements of the ring 200, the soft pad 210 is operable to be hand washed with soap and water. The soft pad 210 is permanently attached to the urethra chamber 206 and is not replaceable. In an alternative embodiment, the soft pad 210 is replaceable.

Figure 6A:
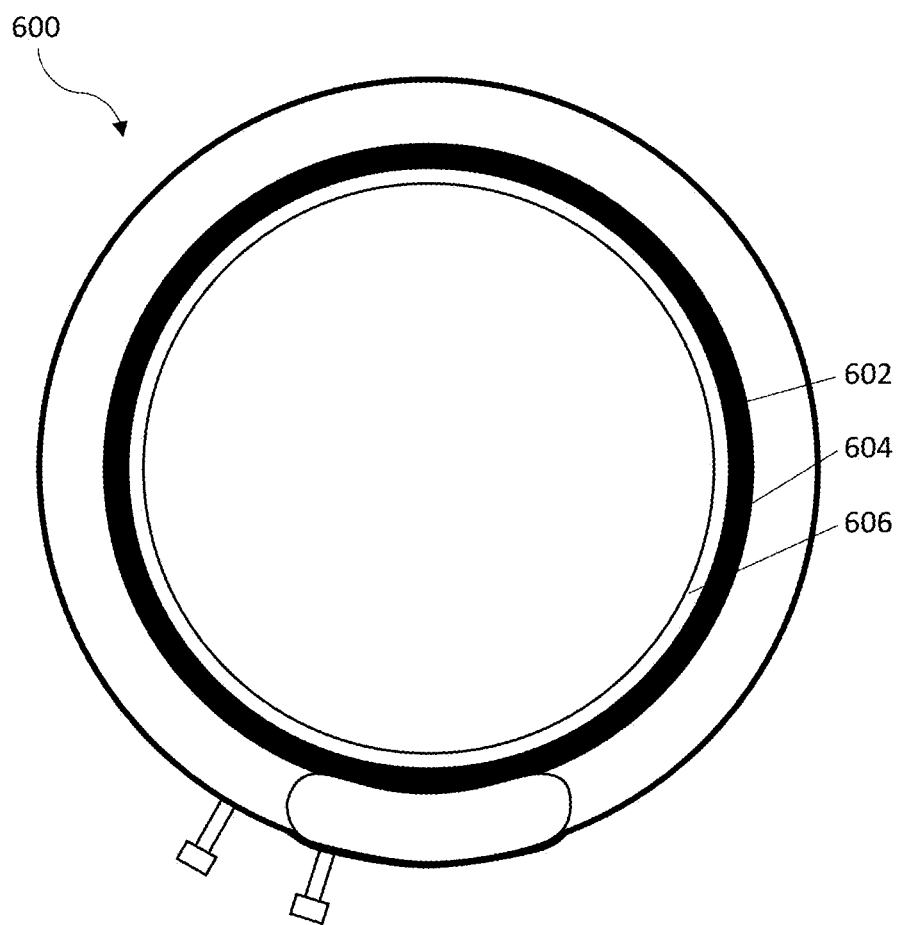
FIG. 6A illustrates a front orthogonal view of a device for managing male urinary incontinence and reducing erectile dysfunction, according to one embodiment of the present invention.
Figure 6B:
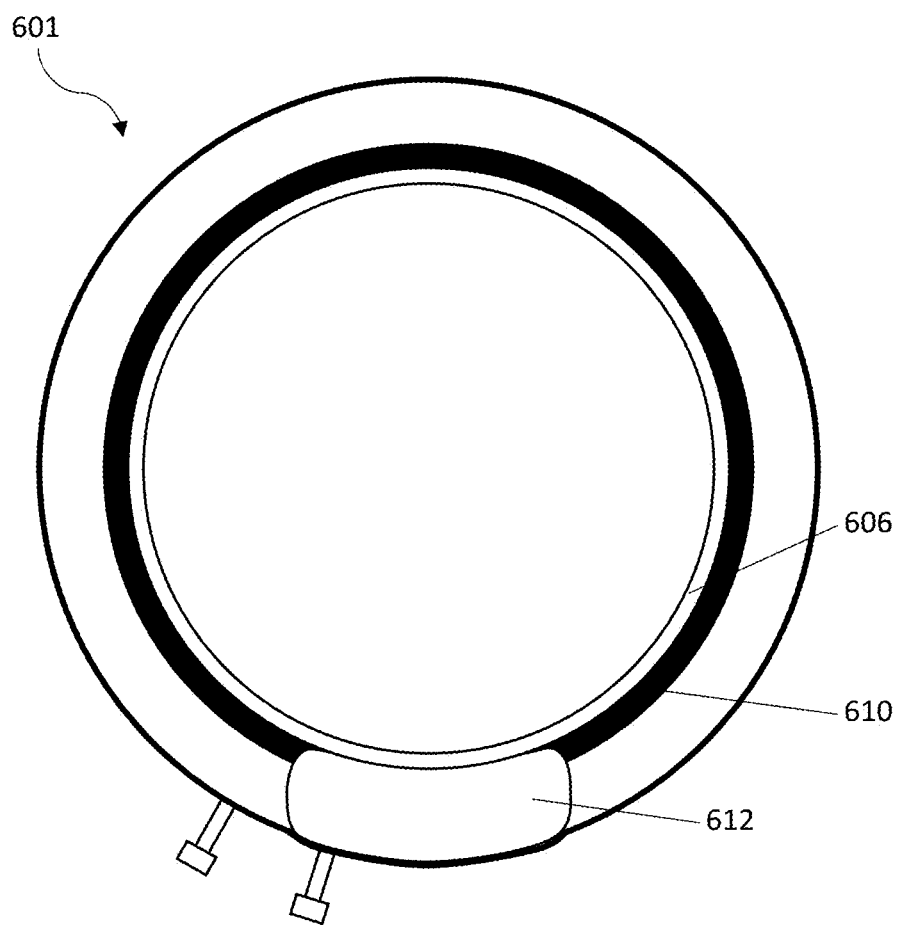
FIG. 6B illustrates a front orthogonal view of a device for managing male urinary incontinence and reducing erectile dysfunction, according to one embodiment of the present invention.

In an alternative embodiment, illustrated by FIG. 6A, the inner layer 602 encircles the entire ring 600, and the inside surface 604 of the inner layer 602 is completely covered by soft pad 606. In yet another embodiment, illustrated by FIG. 6B, the soft pad 606 completely encircles the inside of the ring 601, and the inner layer 610 is interrupted by the urethra chamber 612.

The corpora chamber 204 and the urethra chamber 206 are operable to be inflated by the corpora valve 212 and urethra valve 214, respectively. In one embodiment, a mechanical pump such as medical syringe with a Luer lock mechanism is used to push air through the valves 212 and 214 into the corpora chamber 204 and the urethra chamber 206. In yet another embodiment, valves 212 and 214 are self-inflating. In one embodiment, the valves are quick release valves. The quick release valves are configured to release fluid in the corpora chamber and the urethra chamber and pressure applied on the penis. For example and not limitation, the quick release valves are configured to allow a wearer to eliminate continued application of constrictive pressure and remove the ring. Advantageously, this enables the present invention to meet the requirements of Section 510 of the Federal Food, Drug, and Cosmetic Act. In one embodiment, the vales include a quick release mechanism such as a button, a latch, a cap, and/or a combination of similar mechanisms. In another embodiment, the valves allow a liquid, such as water, or another fluid, to enter the chambers 204 and 206, rather than air. Valves 212 and 214 also make it simple for a user to release the air or liquid in order to deflate the chambers 204 and 206 and release pressure. In one embodiment, the edges of the valves 212 and 214 are pinched to release the contained air or liquid. In another embodiment, a pump is used to remove the contained air or liquid. In another embodiment, the end of the valve opposite the ring 200 is pushed manually by the user, such as with a finger or a sharp object, to release the fluid from the chambers via the valves. Preferably, the valves 212 and 214 are made of a rigid plastic. In another embodiment, the valves 212 and 214 are flexible. In an alternative embodiment, valves 212 and 214 are made of another material, including but not limited to, metal or any other material operable to form a valve. In one embodiment, the corpora valve 212 and urethra valve 214 are not replaceable. In an alternative embodiment, the corpora valve 212 and urethra valve 214 are replaceable. The valves are constructed such that they are easily operable by the user when the device is being set up, in use, being taken off, and once removed. In a preferred embodiment, corpora valve 212 and urethra valve 214 are each about 1 inch long. In another embodiment, corpora valve 212 and urethra valve 214 are each between about 0.5 inches and about 1.5 inches long. In yet another embodiment, corpora valve 212 and urethra valve 214 are no more than about 2.5 inches long. In one embodiment, corpora valve 212 and urethra valve 214 are the same length, and in another embodiment, corpora valve 212 and urethra valve 214 are different lengths in order to be easily identifiable to the user on the basis of touch or sight. In another embodiment, two colors are used to differentiate the corpora valve 212 and urethra valve 214. Alternatively, the corpora valve 212 and urethra valve 214 have different patterns or textures which are used to differentiate between them.

Figure 7:
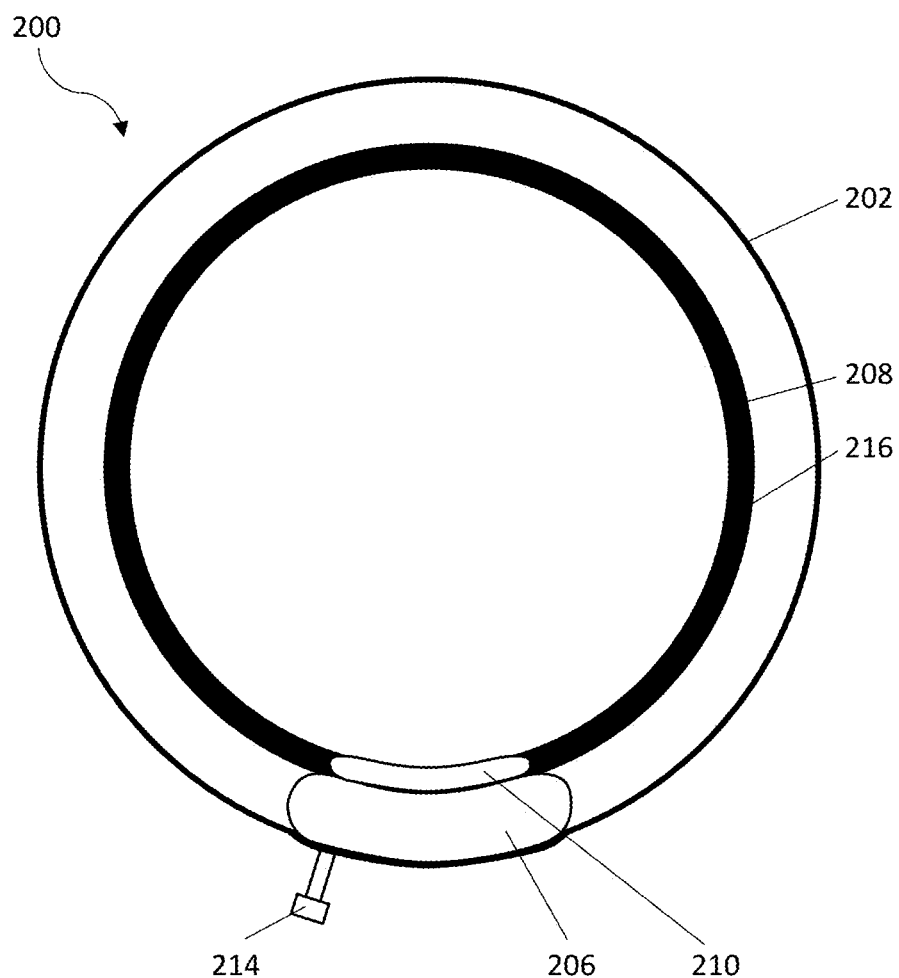
FIG. 7 illustrates a front orthogonal view of a device for managing male urinary incontinence according to one embodiment of the present invention.

FIG. 7 illustrates a device for managing male urinary incontinence according to one embodiment of the present invention. The device is a ring 200 which is comprised of an outer layer 202, a urethra chamber 206, an inner layer 208, a soft pad 210, and a urethra valve 214. The outer layer 202 and the inner layer 208 are concentric circles or an otherwise concentric shape, and the urethra chamber 206 is secured between the outer layer 202 and the inner layer 208. In one embodiment, the inner layer 208 does not make a complete circle, and there is a gap in the inner layer 208 adjacent to the urethra chamber 206. In an alternative embodiment, the gap in the inner layer 208 adjacent to the urethra chamber 206 is filled by the soft pad 210. The urethra chamber 206 is an inflatable and deformable chamber that is operable to be inflated by the urethra valve 214. The ring 200 can be used facing in either direction such that the valve 214 is accessible to either the left or right hand of the user, whichever is preferred. The inner layer 208 is also elastic and deformable. In another embodiment, the outer layer 202 is not expandable and does not expand. The outer layer of the urethral chamber 206 is less expandable than the adjacent soft pad 210 to allow the urethra chamber to expand inwards compressing the soft pad against the urethra to prevent urinary leakage.

Figure 8:
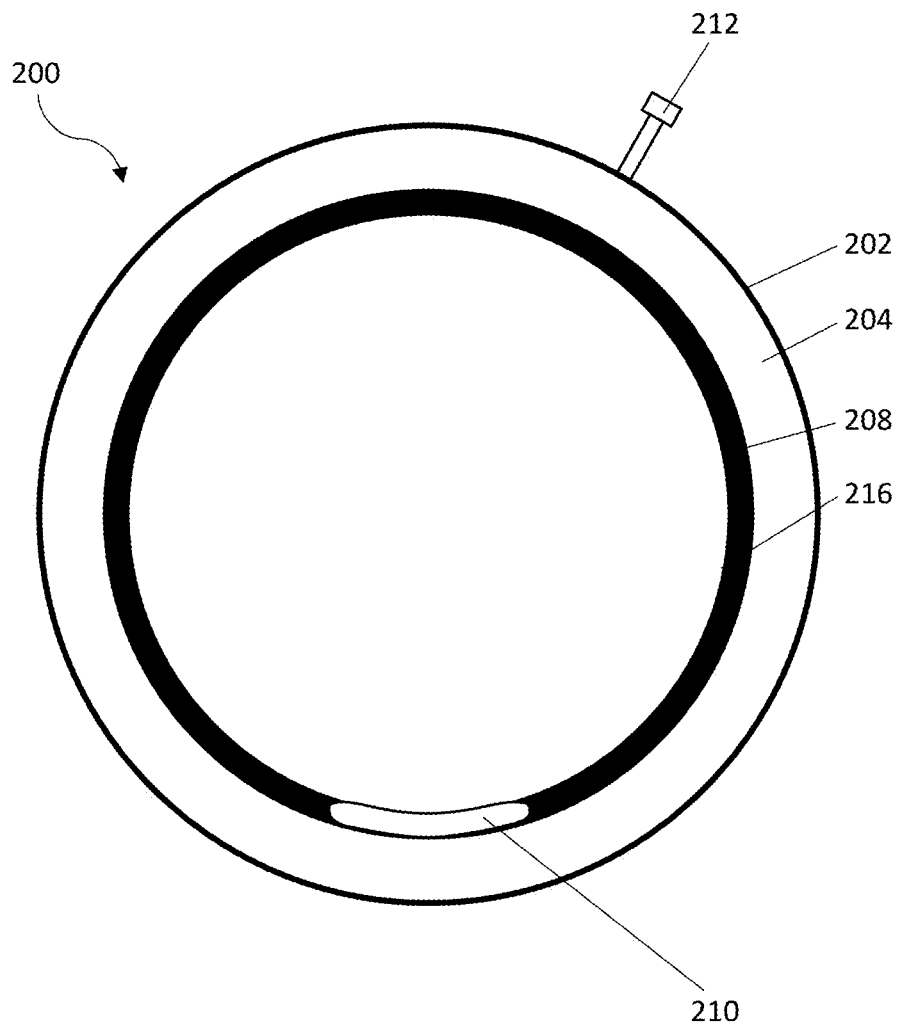
FIG. 8 illustrates a front orthogonal view of a device for reducing erectile dysfunction according to one embodiment of the present invention.

FIG. 8 illustrates a device for reducing erectile dysfunction according to one embodiment of the present invention. The device is a ring 200 which is comprised of an outer layer 202, a corpora chamber 204, an inner layer 208, a soft pad 210, and a corpora valve 212. The outer layer 202 and the inner layer 208 are concentric circles or an otherwise concentric shape, and the corpora chamber 204 is secured between the outer layer 202 and the inner layer 208. In one embodiment, the inner layer 208 does not make a complete circle, and there is a gap in the inner layer 208. The gap in the inner layer 208 is filled by the soft pad 210. Alternatively, the inner layer 208 does make a complete circle. The corpora chamber 204 is an inflatable and deformable chamber which is operable to be inflated by the corpora valve 212. The ring 200 can be used facing in either direction such that the valve 212 is accessible to either the left or right hand of the user, whichever is preferred. The inner layer 208 is also elastic and deformable. The outer layer 202 is less expandable than the inner layer 208, and is also thicker, which forces the corpora chamber 204 to expand inwards when filled with water, air, or another fluid and as such, causes compression on the dorsal veins 112 and 114 to help sustain the erection. In another embodiment, the outer layer 202 is not expandable and does not expand.

The above-mentioned examples are provided to serve the purpose of clarifying the aspects of the invention, and it will be apparent to one skilled in the art that they do not serve to limit the scope of the invention. By nature, this invention is highly adjustable, customizable and adaptable. The above-mentioned examples are just some of the many configurations that the mentioned components can take on. All modifications and improvements have been deleted herein for the sake of conciseness and readability but are properly within the scope of the present invention.

The invention claimed is:

1. A penile compression device comprising:
   a ring configured to fit around a penis;
   wherein the ring includes an outer layer, a corpora chamber, an inner layer, a soft pad, and a corpora valve;
   wherein the corpora chamber is positioned between the outer layer and the inner layer;
   wherein the inner layer encircles the entirety of the ring, wherein an inside surface of the inner layer is completely covered by the soft pad;
   wherein the corpora chamber is inflatable;
   wherein the corpora valve is configured to receive a fluid; and
   wherein the corpora chamber is configured to inflate when the corpora valve receives the fluid.

2. The device of claim 1, wherein the ring is configured to expand to a volume of between about 20 cm³ and about 35 cm³.

3. The device of claim 1, wherein the corpora chamber is configured to create compression on a dorsal vein of the penis when filled with the fluid.

4. The device of claim 1, wherein the soft pad is configured to distribute pressure across a bottom side of the penis.

5. The device of claim 1, wherein the outer layer, the corpora chamber, and the inner layer are a concentric shape.

6. The device of claim 1, wherein the corpora valve includes a quick release mechanism.

7. The device of claim 1, wherein the outer layer is not expandable.

8. The device of claim 1, wherein the inner layer comprises a material, wherein the material includes felt, wool, cotton, polyester, foam, spandex, polyacrylic, polypropylene, silk, velvet, rayon, linen, leather, rubber, and/or silicone.

9. The device of claim 1, wherein the corpora valve is self-inflatable.

10. The device of claim 1, wherein the corpora chamber is configured to create a pressure between about 30 millimeters of mercury and about 120 millimeters of mercury on the penis.

11. A penile compression device comprising:
    a ring configured to fit around a penis;
    wherein the ring includes an outer layer, a urethra chamber, an inner layer, a soft pad, and a urethra valve;
    wherein the urethra chamber is positioned between the outer layer and the inner layer;
    wherein the inner layer includes a gap, wherein the gap is adjacent to the urethra chamber, wherein the gap is operable to receive the soft pad;
    wherein the urethra chamber is inflatable;
    wherein the urethra valve is configured to receive a fluid;
    wherein the urethra chamber is configured to inflate when the urethra valve receives the fluid; and
    wherein the urethra chamber is configured to create compression on the penis near the urethra.

12. The device of claim 11, wherein the outer layer, the urethra chamber, and the inner layer are a concentric shape.

13. The device of claim 11, wherein the urethra valve includes a quick release mechanism.

14. The device of claim 11, wherein the inner layer is configured to tangentially contact the skin of the penis when the urethra chamber is deflated.

15. The device of claim 11, wherein the outer layer is not expandable.

16. The device of claim 11, wherein the urethra chamber in a deflated position and the soft pad are configured to not contact the penis.

17. The device of claim 11, wherein the inner layer comprises a material, wherein the material includes at least one of felt, wool, cotton, polyester, foam, spandex, polyacrylic, polypropylene, silk, velvet, rayon, linen, leather, rubber, and/or silicone.

18. The device of claim 11, wherein the urethra valve is self-inflatable.

19. A penile compression device comprising:
    a ring configured to fit around a penis;
    wherein the ring includes an outer layer, a corpora chamber, a urethra chamber, an inner layer, a soft pad, a corpora valve, and a urethra valve;
    wherein the corpora chamber and the urethra chamber are positioned between the outer layer and the inner layer;
    wherein the inner layer encircles the entirety of the ring, wherein an inside surface of the inner layer is completely covered by the soft pad;
    wherein the corpora chamber and the urethra chamber are inflatable;
    wherein the corpora valve and the urethra valve are configured to receive a fluid via a pump;
    wherein the corpora chamber and the urethra chamber are configured to inflate when the corpora valve and the urethra valve receive the fluid;
    wherein the urethra chamber is configured to put pressure on the penis near the urethra; and
    wherein the corpora chamber is configured to create pressure on a dorsal vein of the penis when filled with the fluid.

20. The device of claim 19, wherein the corpora valve and the urethra value include a quick release mechanism.

* * * * *